US 12,370,331 B2

(12) United States Patent
Selby et al.

(10) Patent No.: US 12,370,331 B2
(45) Date of Patent: *Jul. 29, 2025

(54) CARTRIDGE FOR AN AEROSOL DELIVERY SYSTEM

(71) Applicant: TTP plc, Melbourn (GB)

(72) Inventors: Robert Gordon Maurice Selby, Melbourn (GB); Clennell Douglas Collingwood, Melbourn (GB); Alon Greenenko, Melbourn (GB); Hans-Jürgen Hoppe, Melbourn (GB)

(73) Assignee: TTP LC, Melbourn (GB)

( * ) Notice: Subject to any disclaimer, the term of this patent is extended or adjusted under 35 U.S.C. 154(b) by 1062 days.

This patent is subject to a terminal disclaimer.

(21) Appl. No.: 17/280,332

(22) PCT Filed: Sep. 27, 2019

(86) PCT No.: PCT/EP2019/076288
§ 371 (c)(1),
(2) Date: Mar. 26, 2021

(87) PCT Pub. No.: WO2020/065055
PCT Pub. Date: Apr. 2, 2020

(65) Prior Publication Data
US 2022/0031975 A1    Feb. 3, 2022

(30) Foreign Application Priority Data
Sep. 27, 2018   (EP) .................................... 18197367

(51) Int. Cl.
*A61M 15/00*   (2006.01)
*A61M 15/06*   (2006.01)
(52) U.S. Cl.
CPC ........ *A61M 15/0085* (2013.01); *A61M 15/06* (2013.01)

(58) Field of Classification Search
CPC .............. A61M 15/0085; A61M 15/06; A61M 15/0003; A61M 15/0005; A61M 15/001;
(Continued)

(56) References Cited

U.S. PATENT DOCUMENTS 5,497,763 A * 3/1996 Lloyd ............... A61M 15/0031
128/200.14
5,497,944 A * 3/1996 Weston ................ A61M 11/001
128/200.22
(Continued)

FOREIGN PATENT DOCUMENTS

EP    1317939 A2    6/2003
EP    1552857 A1    7/2005
(Continued)

OTHER PUBLICATIONS

International Search Report, PCT/EP2019/076288, dated May 12, 2019, 4 pages.
(Continued)

*Primary Examiner* — Tu A Vo
*Assistant Examiner* — Kelsey E Baller
(74) *Attorney, Agent, or Firm* — RANKIN, HILL & CLARK LLP

(57) ABSTRACT

A cartridge for an aerosol delivery system. The cartridge includes a fluid reservoir including a first reservoir portion, a second reservoir portion, and at least one liquid barrier configured to separate the first and second reservoir portions. The first and second reservoir portions have respective first and second openings at a first end of the cartridge. The cartridge further includes a perforate membrane located at the first end of the cartridge and over the first and second openings. The first and second openings are configured to supply first and second liquids to a first side of the perforate membrane during use and the perforate membrane includes
(Continued)

a plurality of apertures configured to eject one or both of the first and second liquids from a second side of the perforate membrane in the form of liquid droplets when the perforate membrane is vibrated. An aerosol delivery system includes the cartridge.

18 Claims, 6 Drawing Sheets

(58) Field of Classification Search
CPC ...... A61M 15/0063; A61M 2202/0007; A61M 2202/0488; A61M 2205/0216
USPC .................................................. 128/200.16
See application file for complete search history.

(56) References Cited

U.S. PATENT DOCUMENTS

| | | | | |
|---|---|---|---|---|
| 5,511,538 | A * | 4/1996 | Haber | B05B 11/1091 |
| | | | | 128/200.22 |
| 6,543,443 | B1 | 4/2003 | Klimowicz et al. | |
| 8,382,008 | B1 * | 2/2013 | Ricciardi | G05B 15/02 |
| | | | | 239/338 |
| 2005/0150489 | A1 * | 7/2005 | Dunfield | A61M 15/0083 |
| | | | | 128/200.14 |
| 2005/0263618 | A1 | 12/2005 | Spallek et al. | |
| 2006/0060191 | A1 * | 3/2006 | Yang | A61M 15/0065 |
| | | | | 128/200.14 |
| 2006/0081239 | A1 * | 4/2006 | Alley | A61M 15/00 |
| | | | | 128/200.14 |
| 2007/0256684 | A1 * | 11/2007 | Kelliher | A61M 11/005 |
| | | | | 128/200.14 |
| 2008/0006264 | A1 * | 1/2008 | Gallem | A61M 15/0021 |
| | | | | 128/200.14 |
| 2011/0041844 | A1 * | 2/2011 | Dunne | B05B 1/26 |
| | | | | 128/203.12 |
| 2013/0047986 | A1 | 2/2013 | Goede et al. | |
| 2013/0228191 | A1 * | 9/2013 | Newton | A61M 15/06 |
| | | | | 131/329 |
| 2014/0261488 | A1 | 9/2014 | Tucker | |
| 2015/0151058 | A1 * | 6/2015 | Abate | A61M 15/0021 |
| | | | | 128/200.16 |
| 2017/0333922 | A1 * | 11/2017 | Selby | A61M 11/00 |
| 2018/0020730 | A1 * | 1/2018 | Alarcon | A24F 40/42 |
| | | | | 131/329 |
| 2018/0161796 | A1 * | 6/2018 | Strange | A61M 39/24 |
| 2018/0279678 | A1 * | 10/2018 | Hepworth | A24F 40/42 |

FOREIGN PATENT DOCUMENTS

| | | | | |
|---|---|---|---|---|
| EP | 2390010 A1 * | 11/2011 | .......... | A61M 11/005 |
| FR | 2939616 A1 | 6/2010 | | |
| JP | 2006297325 A * | 11/2006 | | |

OTHER PUBLICATIONS

European Search Report for EP19773471.8, dated Apr. 9, 2024, 5 pages.

* cited by examiner

CARTRIDGE FOR AN AEROSOL DELIVERY SYSTEM

The present invention relates to a cartridge for an aerosol delivery system in which a perforate membrane is used to generate an aerosol. In particular, the present invention relates to a cartridge for an aerosol delivery system, the cartridge having a fluid reservoir. The present invention also relates to aerosol delivery systems including such cartridges.

Aerosol delivery systems that use vibration to generate liquid droplets are well known in the art and have found use in a wide range of fields including medical drug delivery, the treatment of air (for example fragrance delivery and humidification), and used for oral delivery of compounds such as vaccines, for nicotine delivery such as devices similar to e-cigarettes and other active compounds. Some known examples of aerosol delivery systems comprise an aerosol generating device having control electronics and a power supply, such as a battery, coupled to a removable cartridge with a fluid reservoir which is receivable in the aerosol generating device and may be replaced when the fluid in the reservoir has been consumed. In other examples, the aerosol generating system may comprise an aerosol generating device and an integral fluid reservoir, which may be refillable.

International Patent Application Publication No. WO2012/156724 provides a liquid droplet generation apparatus having a perforate membrane, a liquid supply, and an actuator which is connected to the membrane by a magnetic force so that the membrane can be vibrated by the actuator to generate and eject liquid droplets. In another example, International Patent Application Publication No. WO2015/004449 provides an electronic nebulizer having a perforate membrane, a liquid supply, and an actuator which is clamped to the membrane by a releasable mechanical coupling means so that liquid is nebulized through the membrane when the actuator vibrates the membrane. In each case, a perforate membrane with a plurality of apertures is used to generate substantially monodispersed droplets from a liquid supply containing a liquid to be aerosolised.

It would be desirable to provide an improved cartridge for an aerosol delivery system.

According to a first aspect of the present invention, there is provided a cartridge for an aerosol delivery system, the cartridge comprising a fluid reservoir including a first reservoir portion for containing a first liquid, a second reservoir portion for containing a second liquid, and at least one liquid barrier configured to separate the first and second reservoir portions, wherein the first and second reservoir portions have respective first and second openings at a first end of the cartridge, the first and second openings being configured to supply first and second liquids to a perforate membrane located over the first end of the cartridge during use. With this arrangement, different liquids can be stored in the cartridge and ejected by a single membrane.

The cartridge is intended for removable coupling to an aerosol delivery device to form an aerosol delivery system comprising a perforate membrane and an actuation means configured to vibrate the perforate membrane to cause a liquid in the cartridge to pass through the perforate membrane and to be ejected from the perforate membrane as liquid droplets. The provision of such a cartridge allows for easy removal and replacement when one or more liquids in the cartridge have been consumed. The perforate membrane may be provided as part of the cartridge, as an individual component, or as part of an aerosol delivery device with which the cartridge will be used.

Preferably, the cartridge further includes a perforate membrane located at the first end of the cartridge and over the first and second openings such that a first side of the perforate membrane is in fluid communication with the first and second openings, the perforate membrane comprising a plurality of apertures configured to eject one or both of the first and second liquids from a second side of the perforate membrane in the form of liquid droplets when the perforate membrane is vibrated during use. In this embodiment, the perforate membrane is a single membrane which extends over both of the first and second openings.

With this arrangement, the perforate membrane may be easily and regularly replaced in an aerosol delivery system simply by replacement of the cartridge. This can have benefits in terms of maintaining performance of the aerosol delivery system in which the cartridge is used. Keeping the cartridge and the perforate membrane together in this manner can also ensure that the perforate membrane is used with a liquid formulation for which the configuration of its apertures has been specifically designed. This also allows different delivery and fluid characteristics to be selected by the user to suit treatment or preference.

The plurality of apertures may have substantially the same configuration. That is, substantially uniform size, shape, cross-sectional profile and spacing.

Preferably, the plurality of apertures comprises a first array of apertures of a first configuration and a second array of apertures of a second configuration which is different to the first configuration. With this arrangement, the droplets generated by the perforate membrane can have two different size distributions which are generated simultaneously and tuned according to a specific application. For example, the apertures of the first and second arrays can be configured to generate an aerosol having a concentration of droplets of one size, for example small, and a concentration of droplets of a second size, for example large, allowing the aerosol to provide simultaneously the benefits of both droplet sizes. In the case of nicotine delivery to the lungs this can allow the mouth feel and flavour delivery to be tuned independently of uptake in the lung and the level of catch in the throat. For example, by providing a greater number of large droplets, the targeting of taste receptors in the mouth can be increased and by providing a greater number of small droplets, the uptake of medicament in the lungs can be increased.

Furthermore, providing a first array of apertures of a first configuration and a second array of apertures of a second configuration which is different to the first configuration can allow the perforate membrane to be tuned according to the characteristics of different liquid formulations stored in the first and second reservoir portions. This can be particularly beneficial when the first and second liquid formulations have different characteristics, such as viscosity, which lead to the liquid formulations having a different ejection threshold. For example, a more viscous liquid formulation may be used with larger apertures to ensure that a sufficient proportion of the apertures are vibrated above the ejection threshold.

The first and second arrays may at least partially overlap. This means that at least some of the apertures of the first array may be intermingled with at least some of the apertures of the second array. By providing first and second arrays which at least partially overlap, at least some of the smaller droplets generated by one of the arrays will be entrained with the flow of larger droplets generated by the other array. This has been found to delay the evaporation of the smaller droplets and allow them to travel further before entering the gaseous phase. This can allow smaller droplets to enter the lungs in the liquid phase before evaporating into the gaseous phase within the lungs. This can reduce the level of "catch" experienced by the user from droplets being in the gaseous phase in the throat, while still promoting rapid uptake of medicament in the lungs.

The degree of overlap can be determined by determining the area of the first array within a boundary defined by its outermost apertures, determining the area of the second array within a boundary defined by its outermost apertures, determining the area of the region over which the first and second arrays overlap, dividing the area of overlap by the area of the smallest of the first and second arrays and multiplying the product by 100 to obtain the degree of overlap in terms of a percentage. For example, where the smaller of the first and second arrays is entirely within the larger of the first and second arrays, the degree of overlap can be said to be 100 percent.

The degree of overlap may be at least 10 percent, at least 20 percent, at least 30 percent, at least 40 percent, at least 50 percent, at least 60 percent, at least 70 percent, at least 80 percent, or at least 90 percent.

Substantially all of the apertures of at least one of the first and second arrays may be intermingled with the apertures of the other of the first and second arrays.

As used herein, the term "substantially all of the apertures" means at least 95 percent of the total number of apertures of a given array.

The first and second arrays may be substantially coincident. This means that substantially all of the apertures of the first array may be intermingled with substantially all of the apertures of the second array.

The first array of apertures may be located in a first discrete region of the perforate membrane and the second array of apertures is located in a second discrete region of the perforate membrane.

The term "first and second discrete regions" refers to distinct, non-overlapping, areas of the perforate membrane. The discrete regions may be directly adjacent to each other, or separated by an intermediate region.

Typically, the mode of vibration of a perforate membrane in an aerosol delivery system is such that different regions of the membrane vibrate with different amplitudes. This means that the acceleration of the membrane and the fluid pressure generated in those regions can differ. To successfully generate a droplet, an aperture in the perforate membrane needs to be accelerated above a minimum acceleration threshold, or "ejection threshold". Generally, the smaller the aperture, the higher the ejection threshold. Typically, a perforate membrane will have a plurality of apertures having the same configuration. That is, the same size, shape, cross-sectional profile and spacing.

By providing a first array of apertures of a first configuration grouped together in a first discrete region of the membrane and a second array of apertures of a second configuration grouped together in a second discrete region of the membrane, droplet generation from the perforate membrane can be tuned according to the vibration characteristics or vibration pattern of the perforate membrane in the first and second discrete regions. For example, where the amplitude and/or acceleration of vibration in the first discrete region is different to that of the second discrete region and the apertures of the first and second arrays are configured with different sizes, it can be beneficial to place the small apertures in the discrete region with the greatest amplitude and/or acceleration of vibration and to place the large apertures in the discrete region with the lowest amplitude and/or acceleration of vibration. The increased vibrational activity can ensure that a higher percentage of the small apertures are above the ejection threshold. Similarly the larger apertures in a region of lower vibrational activity can also ensure that a higher percentage of the apertures in the less active region are above the ejection threshold. This can increase the utilisation of the membrane and thereby increase the amount of aerosol generated from a given vibrational input and improve the efficiency of the system.

At least one of the first and second arrays may be in fluid communication with both of the first and second reservoir portions. At least one of the first and second reservoir portions may be in fluid communication with both of the first and second arrays.

Preferably, the first reservoir is in fluid communication with the first array of apertures in the first discrete region via the first opening, wherein the first opening is separated from at least some of the second array of apertures in the second discrete region. This means that the first opening is not in fluid communication with at least some of the apertures of the second array. This arrangement allows the apertures of the first array to be tuned specifically according to the characteristics of the liquid formulation stored in the first reservoir portion. Preferably, this separation is performed by the at least one liquid barrier.

Preferably, the first opening is separated from substantially all of the apertures of the second array.

Preferably, the second reservoir is in fluid communication with the second array of apertures in the second discrete region via the second opening, and wherein the second opening is separated from at least some of the apertures of the first array in the first discrete region. This means that the second opening is not in fluid communication with at least some of the apertures of the first array. This arrangement allows the apertures of the second array to be tuned specifically according to the characteristics of the liquid formulation stored in the second reservoir portion. Preferably this separation is performed by the at least one liquid barrier.

Preferably, the second opening is separated from substantially all of the apertures of the first array.

Typically, the mode of vibration of a perforate membrane is such that different regions of the membrane vibrate with different amplitudes. This means that the acceleration of the membrane and the fluid pressure generated in those regions can differ. To successfully generate a droplet, an aperture in the perforate membrane needs to be accelerated above a minimum acceleration threshold, or "ejection threshold". Generally, the smaller the aperture, the higher the ejection threshold.

The first and second discrete regions may be located in regions of the perforate membrane having comparable vibration characteristics, for example similar amplitude and/or acceleration.

Preferably, the first discrete region is located in a region of the perforate membrane having a first vibration characteristic and the second discrete region is located in a region of the perforate membrane having a second vibration characteristic which is different to the first vibration characteristic, such that vibration of the perforate membrane during use causes the first discrete region to vibrate at a different amplitude to the second discrete region.

With this arrangement, droplet generation from the perforate membrane can be tuned according to the vibration characteristics or vibration pattern of the perforate membrane in the first and second discrete regions. For example, where the apertures of the first and second arrays are configured with different sizes, it can be beneficial to place the small apertures in the discrete region with the greater vibrational activity and to place the large apertures in the discrete region with the lower vibrational activity. The increased vibrational activity can ensure that a higher percentage of the small apertures are above the ejection threshold. Similarly having larger apertures in a region of lower vibrational activity can also ensure that a higher percentage of the apertures in the less vibrationally active region are above the ejection threshold. This can increase the utilisation of the membrane and thereby increase the amount of aerosol generated from a given vibrational input and improve the efficiency of the system.

The first and second vibration characteristics of the perforate membrane may be such that vibration of the perforate membrane by the actuation means causes the first discrete region to vibrate at a greater amplitude than the second discrete region.

The first and second discrete regions may be located in regions of the perforate membrane having low vibration activity.

At least one of the first and second discrete regions may be located in or adjacent to an excitation region of the perforate membrane in which the amplitude of vibration during use is greater than the average amplitude of vibration of the perforate membrane. Both of the first and second discrete regions may be located in or adjacent to an excitation region of the perforate membrane. At least one of the first and second discrete regions may be located in or adjacent to a maximum excitation region of the perforate membrane in which the amplitude of vibration during use is at the maximum value.

The first and second discrete regions may both be located towards the periphery of the perforate membrane. Preferably, at least one of the first and second discrete regions is located in or adjacent to a central region of the perforate membrane. For example overlapping with the central region, or entirely within the central region.

The term "central region" refers to the area of the perforate membrane which is centred on the centroid of the perforate membrane. The central region may have an area of less than 50 percent of the total area of the perforate membrane, preferably less than 30 percent, more preferably less than 20 percent, most preferably less than 10 percent of the total area of the perforate membrane.

Optionally, both of the first and second discrete regions may be located in or adjacent to the central region of the perforate membrane.

The first and second discrete regions may be approximately equidistant from the centroid of the perforate membrane.

In certain embodiments, the first discrete region is located in or adjacent to the central region and the second discrete region is located peripherally of the first discrete region. For example, the second discrete region may be disposed around the first discrete region. The second discrete region may substantially circumscribe the first discrete region. The second discrete region may form an annulus around the first discrete region.

The plurality of apertures of the first and second arrays may have substantially the same size. That is, the average size of the apertures of the first array may be within 10 percent, preferably 5 percent, of the average size of the apertures of the second array. The first and second arrays may be configured such that at least 60 percent, at least 70 percent, at least 80 percent, preferably at least 90 percent of the apertures of the first array are within the same size range as at least 60 percent, at least 70 percent, at least 80 percent, preferably at least 90 percent of the apertures of the second array. Where the plurality of apertures of the first and second arrays have substantially the same size, the configurations of the apertures of the first and second arrays may differ in other aspects, for example in shape, spacing, or profile in order to generate different droplet sizes.

In certain preferred embodiments, the apertures of the first array are of a first aperture size and the apertures of the second array are of a second aperture size, wherein the first and second aperture sizes are different. This has been found to provide a particularly effective means by which different droplet size distributions can be generated.

The terms "first and second aperture size" refer to the average size of the apertures of the first and second arrays, respectively. Preferably, at least 60 percent, at least 70 percent, at least 80 percent, more preferably at least 90 percent of the apertures of the first array have a size which is within 10 percent, preferably 5 percent of the first aperture size. Preferably, at least 60 percent, at least 70 percent, at least 80 percent, more preferably at least 90 percent of the apertures of the second array have a size which is within 10 percent, preferably 5 percent, of the second aperture size.

The first aperture size may be greater than the second aperture size. Preferably, the first aperture size is less than the second aperture size.

The term "aperture size" may refer to any objective size measurement. For example, maximum diameter, minimum diameter, surface area, circumference, or hydraulic diameter. Further, the term "aperture size" may refer to the dimensions of the aperture on the first side of the perforate membrane, or on the second side.

Preferably, the term "aperture size" refers to the hydraulic diameter on the second side of the perforate membrane. This has been found to be a key factor in the size of droplets generated by a given aperture.

Preferably, the apertures of the first array have a first average hydraulic diameter at the second side of the perforate membrane and the apertures of the second array have a second average hydraulic diameter at the second side of the perforate membrane, and wherein the second average hydraulic diameter is greater than the first average hydraulic diameter. The second average hydraulic diameter is preferably at least 10 percent greater, more preferably at least 30 percent greater, most preferably at least 50 percent greater than the first average hydraulic diameter.

Preferably, a majority of the apertures of the first array each have a hydraulic diameter at the second side of the perforate membrane of less than 15 microns, more preferably less than 10 microns, most preferably less than 5 microns. Preferably a majority of the apertures of the first array each have a hydraulic diameter at the second side of the perforate membrane of at least 0.5 microns, more preferably at least 1 micron, most preferably at least 2 microns. For example, at least 2 microns and less than 5 microns. The term "majority of the apertures" refers to a population of greater than 50 percent of all apertures of the first array. In certain embodiments, at least 60 percent, at least 70 percent, at least 80 percent, or at least 90 percent of the apertures of the first array may each have a hydraulic diameter at the second side of less than 15 microns, more preferably less than 10 microns, most preferably less than 5 microns. In certain embodiments, at least 60 percent, at least 70 percent, at least 80 percent, or at least 90 percent of the apertures of the first array may each have a hydraulic diameter at the second side of the perforate membrane of at least 0.5 microns, more preferably at least 1 micron, most preferably at least 2 microns. For example, at least 2 microns and less than 5 microns. This has been found to be particularly effective at generating droplet sizes of 5 microns and below. Such droplet sizes have been found to be beneficial in allowing the droplets to reach the lung without impact the throat. Once the droplets have passed the throat, then rapid evaporation into the gaseous phase allows a high rate of uptake of the medicament while minimising the total quantity of medicament required for that uptake.

Preferably, a majority of the apertures of the second array each have a hydraulic diameter at the second side of at least 5 microns, preferably from 5 microns to 60 microns, more preferably from 5 microns to 50 microns, most preferably from 5 microns to 15 microns.

The term "majority of the apertures" refers to a population of greater than 50 percent of all apertures of an array. The term may refer to at least 60 percent, at least 70 percent, at least 80 percent, or at least 90 percent of the apertures of that array.

In certain embodiments, at least 60 percent, at least 70 percent, at least 80 percent, or at least 90 percent of the apertures of the second array may each have a hydraulic diameter at the second side of at least 5 microns, preferably from 5 microns to 60 microns, more preferably from 5 microns to 50 microns, most preferably from 5 microns to 15 microns. This has been found to be particularly effective at generating droplet sizes of 10 microns or larger, for example up to 30 microns in diameter.

The apertures of one or both of the first and second arrays may be spaced from an adjacent aperture by less than 75 microns, for example less than 65 microns. This has been found to promote coalescence and thereby promote the targeted delivery of larger droplets from the array to the user's mouth.

A majority of the apertures of the first and second arrays may be spaced, at the second side of the perforated membrane, from any adjacent aperture by at least 65 microns, for example at least 75 microns. This spacing has been found to reduce the extent to which ejected droplets tend to coalesce downstream of the perforate membrane. This can reduce the diversity in droplet size and ensure targeted delivery of droplets.

The plurality of apertures of the first array may be evenly or unevenly spaced. The plurality of apertures of the second array may be evenly or unevenly spaced.

A majority of the apertures of the first array may be spaced, at the second side of the perforate membrane, from any adjacent aperture by a first spacing and a majority of the apertures of the second array may be spaced, at the second side of the perforate membrane, from any adjacent aperture by a second spacing. The second spacing may be different to the first spacing. This can enhance the difference between droplet sizes generated by the first and second arrays and can, therefore, enhance the degree to which droplet sizes can be tuned according to the specific application.

As used herein, the terms "spaced" and "spacing" refer to the minimum distance between the outer edges of two adjacent apertures in the plane of the perforate membrane.

Varying the spacing between apertures can allow some droplets to coalesce into larger droplets while allowing other droplets to continue as individual droplets. As with the provision of different sized apertures, this allows different size droplets to be generated by the aerosol delivery system. This can allow the mouth feel and flavour delivery to be tuned independently of uptake in the lung and the level of catch in the throat. Coalescence from closely spaced holes tends to occur within 10 millimetres of the ejection from the perforate membrane and so is well established before the droplets enter the user's mouth and throat.

Preferably the first spacing is at least 65 microns, preferably at least 75 microns. This has been found to reduce the occurrence of coalescence and promote the delivery of smaller droplets from the first array. Preferably, the second spacing is less than 75 microns, preferably less than 65 microns. This has been found to promote coalescence and thereby promote the delivery of larger droplets.

The at least one liquid barrier may comprise a rigid seal. Preferably, the at least one liquid barrier comprises a resilient seal. The resilient seal may be in contact with the first side of the perforate membrane. The provision of a resilient seal can improve the effectiveness of the seal formed between the first and second reservoir portions and thereby reduce the extent to which first and second liquids in the first and second liquid portions come into contact with each other prior to ejection from the perforate membrane. This can increase the shelf life of the cartridge. This can also improve the consistency of aerosol properties by ensuring that each liquid is ejected from the correct region of the perforate membrane.

Preferably, at least one of the first and second reservoir portions comprises a porous carrier material adjacent to the perforate membrane. With this arrangement, the liquid formulation can be held in close proximity to the perforate membrane independent of the orientation of the cartridge or aerosol delivery device within which the cartridge is received. The porous carrier material may be in contact with the first side of the perforate membrane. Each of the first and second reservoir portions may comprise a porous carrier material adjacent to the perforate membrane.

The first and second reservoir portions may be positioned side-by-side. Preferably, one of the reservoir portions is annular and defines a cavity within which the other reservoir portion is disposed. Preferably, the second reservoir portion is annular and defines a cavity, and the first reservoir portion is disposed in the cavity defined by the second reservoir portion. The first reservoir portion may extend along the central axis of the second reservoir portion so that the first opening is adjacent to the centre of the perforate membrane.

The first reservoir portion may contain any suitable liquid formulation. The first reservoir portion may contain a first liquid formulation comprising a biologically active ingredient. The first reservoir portion may contain a first liquid formulation comprising a flavourant. Preferably, the first reservoir portion contains a liquid formulation comprising nicotine. Alternatively, or in addition, the first reservoir portion may contain a liquid formulation comprising biologically active molecules in solvents, and/or biologically active molecules held in and on carrier systems. Carriers may be particulates of inorganic and organic materials. Carriers may be viral capsids or entities designed to mimic viral capsids.

The second reservoir portion may contain any suitable liquid formulation. The second reservoir portion may contain a second liquid formulation comprising a biologically active ingredient. The second reservoir portion may contain a second liquid formulation comprising a flavourant. Preferably, the second reservoir contains a liquid formulation comprising one or more flavour compounds. For example, biologically active molecules in solvents, and/or biologically active molecules held in and on carrier systems. Carriers may be particulates of inorganic and organic materials. Carriers may be viral capsids or entities designed to mimic viral capsids.

Where the first and/or second reservoir portions contain a liquid formulation comprising biologically active molecules, the biologically active molecules may be small molecules with molecular mass of less than 1000 daltons; may be small molecules with molecular mass of less than 2000 daltons; molecules may be biologically derived macromolecules such as proteins and nucleic acids; molecules may be polymeric materials; molecules may be systems with long chain backbones or branched chain systems such as denrimers—for example with peptide, sugar phosphate, polyethylene oxide polysaccharide or other sugar; length of polymeric backbone may be from 2 units to many units. Molecules may be fusions of the above where more than one molecule may be formulated or covalently bound together.

According to a second aspect of the present invention, there is provided an aerosol delivery system comprising: a cartridge according to the first aspect; an aerosol delivery device with which the cartridge is configured to be removably coupled; and a perforate membrane located at the first end of the cartridge and over the first and second openings such that a first side of the perforate membrane is in fluid communication with the first and second openings, wherein the perforate membrane comprises a plurality of apertures, and wherein the aerosol delivery device comprises actuation means configured to vibrate the perforate membrane to cause first and second liquids in the first and second reservoirs to be ejected as liquid droplets from a second side of the perforate membrane.

The perforate membrane may be provided as part of the aerosol delivery device or as an individual removable component. Preferably, the perforate membrane forms part of the removable cartridge. With this arrangement, the perforate membrane may be easily and regularly replaced along with the removable cartridge. This can have benefits in terms of maintaining performance. Keeping the cartridge and the perforate membrane together in this manner can ensure that the perforate membrane is used with a liquid formulation for which the configuration of its apertures has been specifically designed.

Features described in relation to one aspect of the invention may also be applicable to another aspect of the invention. In particular, features described in relation to the removable cartridge of the first aspect may be applicable to the aerosol delivery system of the second aspect.

The invention will now be further described, by way of example only, with reference to the accompanying drawings, in which.

Figure 1:
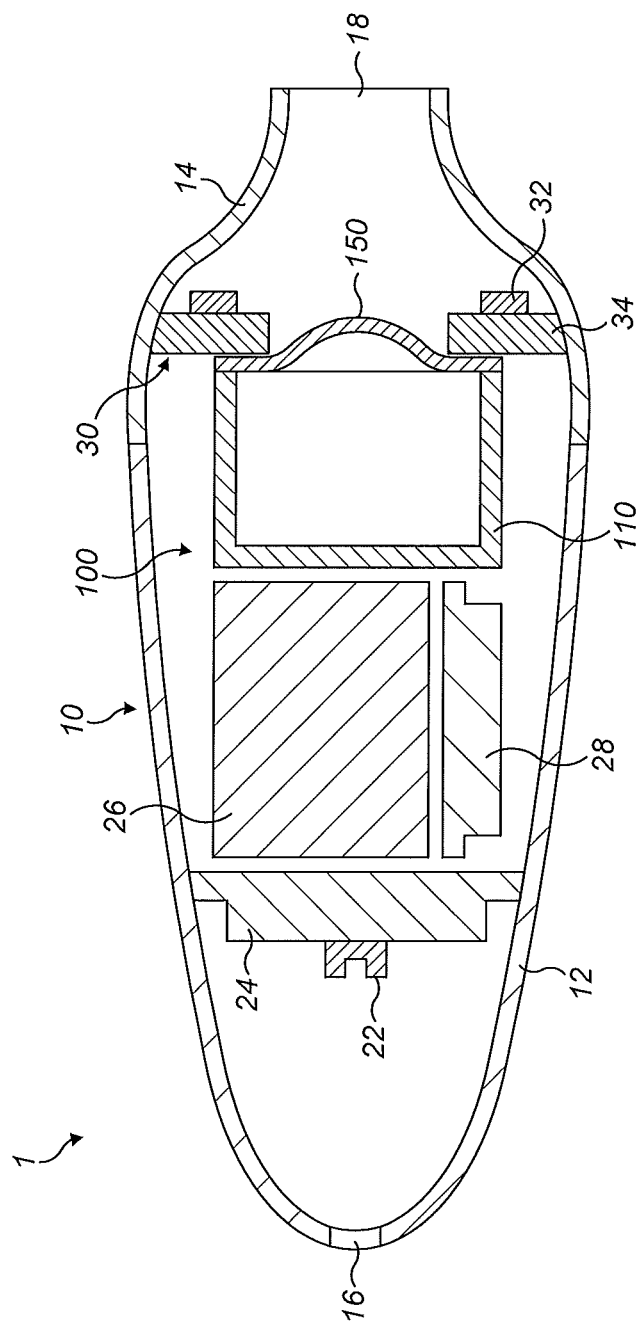
FIG. 1 shows a schematic representation of an aerosol delivery system including a removable cartridge according to a first embodiment.

FIG. 1 shows a schematic representation of an aerosol delivery system 1 comprising a handheld, portable aerosol delivery device 10 and a removable cartridge 100 according to a first embodiment of the invention. The aerosol delivery device 10 comprises a main housing 12 and a mouthpiece 14 which is removably coupled to the main housing 12 to define a chamber within which the cartridge 100 is removably received during use. An air inlet 16 is provided at a distal end of the main housing 12 and the mouthpiece 14 defines an air outlet 18 at the proximal end of the device 10. An airflow pathway extends through the device 10 between the air inlet 16 and the air outlet 18. Also included in the device 10 is a flow sensor 22, preferably mounted on a printed circuit board (PCB) 24, a controller 2, a battery 28 and an actuation means 30 adjacent to the cartridge 100. The PCB 24 and the controller 26 are shown schematically in FIG. 1 as different components. However, they could be combined into a single component. For example, one PCB including the sensor and the controller. The battery 28 supplies electrical power to the PCB 24, the controller 26 and the actuation means 30. The actuation means 30 may comprise any suitable actuator 32 or vibrator element but it is of particular benefit if the actuation means comprises an actuator that has an active component comprising a piezoelectric, electrostrictive or magnetostrictive material (i.e. a material that changes shape in response to an applied electric or magnetic field) in combination with a passive component by which the active component is supported. In this example, the actuation means 30 comprises a lead zirconate titanate (PZT) ceramic active component 32, which is bonded to a passive substrate 34. The actuation means may have any suitable shape. In this example, the actuation means is planar and annular.

The cartridge 100 includes an outer casing 110 defining a fluid reservoir containing a liquid formulation for aerosolisation and having an opening at a first end of the cartridge, and a perforate membrane 150 mounted across the opening such that a first side of the perforate membrane 150 is in fluid contact with the liquid formulation in the fluid reservoir and such that a second, opposite side of the perforate membrane 150 is facing the air outlet 18 in the mouthpiece 14. The fluid reservoir may include a porous carrier material (not shown) by which the liquid formulation is delivered to the perforate membrane 150 by capillary action. Alternatively, the liquid formulation may be delivered to the perforate membrane under the action of gravity or through other capillary means such as a capillary plate located close to the first face of the perforate membrane so as to hold liquid in contact with the perforate membrane. The actuation means 30 is removably coupled to the cartridge 100 such that vibration of the actuation means 30 is transferred to the cartridge 100. The removable coupling (not shown) also allows the cartridge 100 to be exchanged when empty or when a different formulation is required. Any suitable coupling may be used. For example, the coupling can be mechanical, bayonet, compression fit, magnetic coupling, or any combination thereof. In this example, the actuation means is coupled to the cartridge by a magnetic coupling.

In use, when a user inhales on the mouthpiece 14, air is drawn into the device 10 through the air inlet 16 and along the airflow pathway to trigger the flow sensor 22 which sends a signal to the controller 24. The controller 24 then generates a drive signal to drive the actuation means 30 to vibrate and induce vibration in the perforate membrane 150. Vibration of the perforate membrane 150 causes the liquid formulation to pass through apertures in the perforate membrane 150 and to be ejected as liquid droplets from a second side of the perforate membrane 150. The droplets are fed into the air stream flowing along the airflow pathway to form an aerosol, which can be inhaled by the user via the mouthpiece 14. For details of the operation of the device 10, along with suitable actuator design and coupling of the actuation means to the perforate membrane, reference is made to WO 2015/004449 in which these aspects are described in detail. The configuration of the apertures in the perforate membrane is discussed below in relation to FIGS. 6 to 9.

Figure 2:
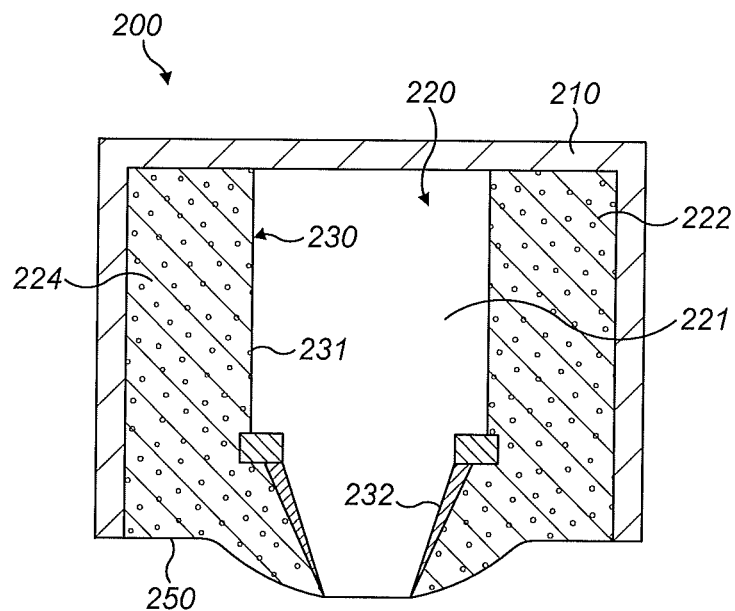
FIG. 2 shows a schematic cross-sectional view of a second embodiment of removable cartridge for the aerosol delivery system of FIG. 1.

FIG. 2 is a schematic cross-sectional view of a removable cartridge 200 according to a second embodiment. As with the first embodiment of cartridge 100, the cartridge 200 includes an outer casing 210 defining a fluid reservoir 220 with an opening at the first end of the cartridge, and a perforate membrane 250 across the opening in the fluid reservoir 220. When the perforate membrane 250 is vibrated, a liquid formulation in contact with the first side of the perforate membrane 250 can be drawn through apertures in the perforate membrane 250 and ejected as liquid droplets from the second side of the perforate membrane 250. The fluid reservoir 220 includes a first reservoir portion 221 for containing a first liquid formulation, a second reservoir portion 222 for containing a second liquid formulation, and a liquid barrier 230 configured to separate the first and second reservoir portions 221, 222. The liquid barrier 230 extends along the length of through the fluid reservoir 220 from a base of the casing 210 at the second end of the cartridge to the perforate membrane 250 to separate the first and second reservoir portions. The first and second reservoir portions have respective first and second openings at the first end of the cartridge. The first and second openings are configured to allow fluid communication between the perforate membrane and the first and second reservoir portions so that first and second liquids in the first and second reservoir portions can be delivered to the membrane during use.

The second reservoir portion 222 comprises a porous carrier material 224 in which the second liquid formulation may be absorbed and retained. The porous carrier material 224 is in contact with the first side of the perforate membrane 250 so that the second liquid formulation can be delivered to the first side of the perforate membrane 250 by capillary action. The porous carrier material may be formed from any suitable material or materials. For example, the porous carrier material may comprise open-cell foam such as polyurethane foam, polyvinyl alcohol (PVA) foam, polyether foam or a combination of foams, a felt material such as polypropylene, polyester, or rayon, a filter material such as polypropylene or a fibrous material such as polyester material in woven or non-woven forms. The porous material could be provided by a sequence of moulded channels of such size that capillary action will retain fluid. The preferred material should have appropriate pore size or capillary channel size to retain the operating fluid and should have properties that are compatible with the fluid (chemical resistance) non contaminating (extractables and leachables) and non-binding such that the target fluid or in particular the active component does not preferentially adhere to the material and so inhibit delivery.

The first and second reservoir portions may have any suitable shape. In this example, the second reservoir portion 222 is annular and defines a cavity extending along its central axis in which the first reservoir portion 221 and the liquid barrier 230 are disposed.

In this example, the liquid barrier 230 comprises a barrier wall 231 extending from the base of the fluid reservoir 220 at its first end, and having a flexible seal 232 at its second end. The flexible seal 232 contacts the first side of the perforate membrane 250 and is configured to ensure that the first and second reservoir portions 221, 222 are separated even when the perforate membrane is vibrated. The flexible seal 232 is preferably a resilient seal. With this arrangement, when the flexible seal 232 is deflected by vibration of the perforate membrane 250, the flexible seal 232 is pressed against the first side of the perforate membrane 250 to improve sealing between the liquid barrier 230 and the perforate membrane 250. This can reduce the extent to which first and second liquid formulations might mix prior to aerosolisation by passing around the upper end of the liquid barrier 230, particularly during vibration of the perforate membrane 250. As shown in FIG. 2, the flexible seal 232 preferably tapers inwardly towards the perforate membrane 250. This can reduce the force required for the perforate membrane 250 to deflect the flexible seal 232 and so minimise the impact that the flexible seal has on the deflection of the perforate membrane during operation. Where the perforate membrane 250 includes first and second arrays of apertures arranged in first and second discrete regions of the perforate membrane 250, as discussed in more detail below, the liquid barrier 230 is preferably configured to separate the first and second discrete regions on the first side of the perforate membrane. With this arrangement, the first liquid formulation is ejected only from the first array of apertures and the second liquid formulation is ejected only from the second array of apertures.

Figure 3:
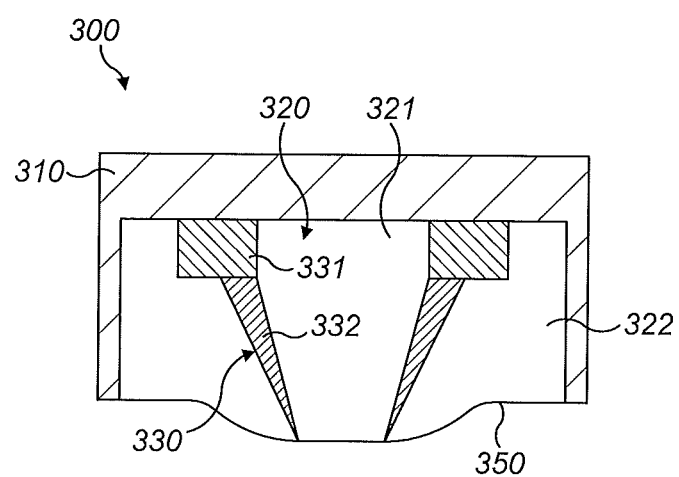
FIG. 3 shows a schematic cross-sectional view of a third embodiment of removable cartridge for the aerosol delivery system of FIG. 1.

FIG. 3 is a schematic cross-sectional view of a removable cartridge 300 according to a third embodiment. The removable cartridge 300 of the third embodiment is similar in construction and operation to the cartridge 200 of the second embodiment and similar reference numerals are used to denote similar components. Thus, the removable cartridge 300 comprises a fluid reservoir 320 which includes a first reservoir portion 321 for containing a first liquid formulation, a second reservoir portion 322 for containing a second liquid formulation, and a liquid barrier 330 configured to separate the first and second reservoir portions 321, 322. The liquid barrier 330 comprises a barrier wall 331 extending from the base of the fluid reservoir 320 at its first end and having a flexible seal 332 at its second end. However, unlike the cartridge 200 of the second embodiment, neither of the first and second reservoir portions 321, 322 of the removable cartridge 300 of the third embodiment contain a porous carrier material. Instead, fluid contact is maintained with the perforate membrane 350 through orientation of the cartridge of through geometric considerations. For example, where the volume of one or both reservoir portions is relatively small, fluid contact with the membrane can be maintained by capillary action which dominates gravitational forces for smaller volumes. Where the volume of the reservoir portions is larger and the geometry of the reservoir portions is wider, gravitational forces dominate capillary forces and fluid contact with the perforate membrane 350 can be maintained under gravity by inverting the cartridge.

Figure 4:
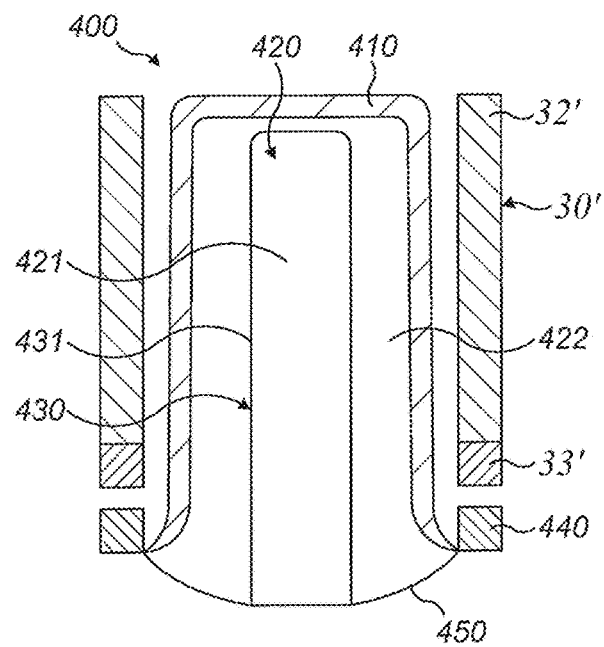
FIG. 4 shows a schematic cross-sectional view of a fourth embodiment of removable cartridge for the aerosol delivery system of FIG. 1.

FIG. 4 is a schematic cross-sectional view of a removable cartridge 400 according to a fourth embodiment. The removable cartridge 400 of the fourth embodiment is similar in construction and operation to the cartridge 300 of the third embodiment and similar reference numerals are used to denote similar components. However, unlike the cartridge 300 of the third embodiment, instead having a liquid barrier comprising a barrier wall and a resilient seal which presses against the membrane, the liquid barrier 430 of the removable cartridge 400 of the fourth embodiment comprises a flexible divider 431 which is fixed to the first side of the perforate membrane 450 to form a seal. The cartridge 400 also includes a magnetic element 440 around the casing 410 by which the perforate membrane 450 can be magnetically coupled to a magnetic ring 33' bonded on the end of the actuator 32' of the actuation means 30'. The magnetic element 440 may be annular and may comprise any suitable magnetic material. For example, the magnetic element 440 may be a Neodymium magnet ring.

Figure 5:
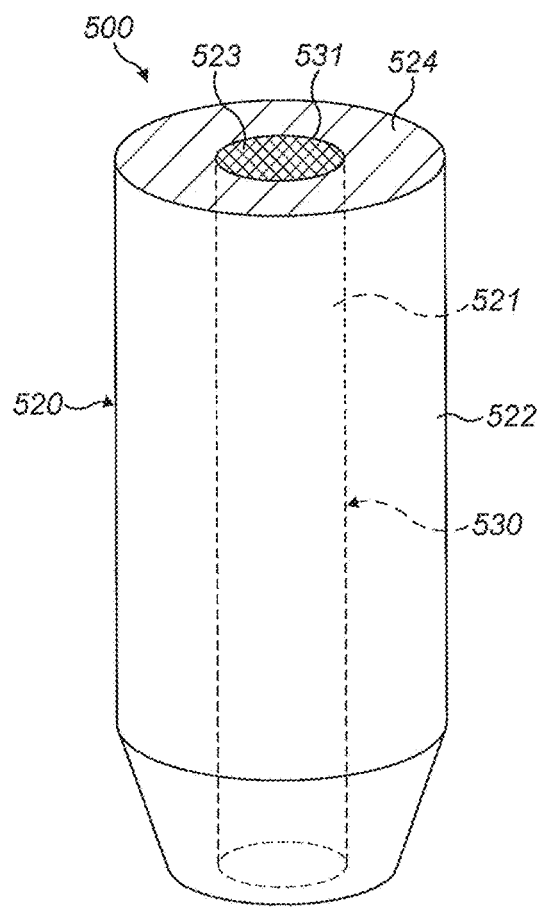
FIG. 5 shows a perspective view illustrating a fifth embodiment of removable cartridge for the aerosol delivery system of FIG. 1, in which the casing and membrane of the removable cartridge are not shown.

FIG. 5 is a perspective view illustrating a removable cartridge 500 according to a fifth embodiment, in which the casing and membrane are not shown. As with the cartridges 200, 300, 400 of the second, third, and fourth embodiments, the cartridge 500 has a fluid reservoir 520 including a first reservoir portion 521 for containing a first liquid formulation, a second reservoir portion 522 for containing a second liquid formulation, and a liquid barrier 530 configured to separate the first and second reservoir portions 521, 522. The first reservoir portion 522 includes a first porous carrier material 523 in which the first liquid formulation may be absorbed and retained. The second reservoir portion 522 includes a second porous carrier material 524 in which the second liquid formulation may be absorbed and retained. The porous carrier materials 522, 524 are both in contact with the first side of the perforate membrane 550 so that the first and second liquid formulations can be delivered to the first side of the perforate membrane 550 by capillary action. The second reservoir portion 522 is annular and defines a cavity extending along its central axis in which the first reservoir portion 521 and the liquid barrier 530 are disposed. The liquid barrier 530 comprises a barrier wall 531 around the first carrier material 523 of the first reservoir portion 521. The barrier wall 531 may be an individual component, or a coating applied to the outer surface of the first carrier material 523 and/or the inner surface of the second carrier material 524.

Figure 6:
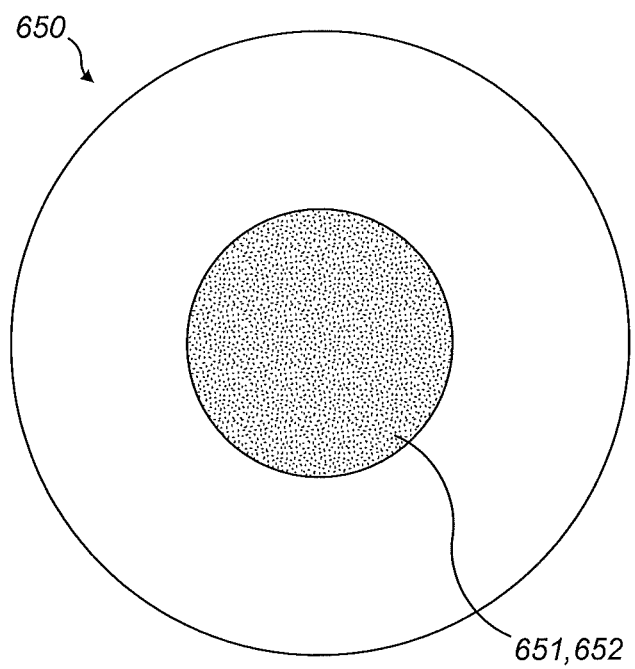
FIG. 6 shows a schematic end view of a first embodiment of perforate membrane for the aerosol delivery system of FIG. 1 or for the cartridges of any of FIGS. 2 to 5.

FIG. 6 is a schematic end view of a first embodiment of perforate membrane 650 comprising a plurality of apertures extending through the thickness of the membrane. The plurality of apertures comprises a first array 651 of apertures having a first aperture size and a second array 652 of apertures having a second aperture size which is larger than the first aperture size. Preferably, the apertures of the first array have an average hydraulic diameter of less than 5 microns, for example in the range of 2 to 5 microns. This generates droplets of 5 microns or less in diameter. Such droplets have been found to be beneficial for uptake of medicament in the lungs of a user for a given flow rate. Preferably, the apertures of the second array have an average hydraulic diameter of at least 5 microns, preferably from 5 microns to 15 microns. This has been found to be particularly effective at generating droplet sizes of 10 microns or larger, for example up to 30 microns in diameter. Such droplet sizes have been found to be beneficial for flavour delivery and mouth feel.

In this example, the first and second arrays are substantially coincident in the central region of the perforate membrane. This means that the two arrays overlap to form a mixed region of apertures in which substantially all of the apertures of the first array are intermingled with substantially all of the apertures of the second array. With this arrangement, the smaller droplets generated by the first array are entrained with the flow of larger droplets generated by the second array. Small amounts of evaporation from the larger droplets will saturate and cool the surrounding air and greatly reduce evaporation of the entrained smaller droplets. The large droplets thus act as a buffer to delay evaporation of the smaller droplets, allowing the smaller droplets to travel further before entering the gaseous phase. In the case of delivery to the lung, the change in air flow direction between the mouth and the throat may allow separation of the two droplet size distributions so that the small droplets can continue into the lungs while the larger droplets will be deposited in the mouth and throat and thereby target taste receptors in the mouth. Once in the lungs, the small droplets can evaporate into the gaseous phase for rapid uptake of the medicament in the first liquid. Preferably, the majority of the apertures of both of the first and second arrays are spaced from any adjacent aperture by at least 65 microns, preferably at least 75 microns, to reduce the tendency of droplets to coalesce downstream of the perforate membrane and to maintain the droplet size distribution substantially as generated by the first and second arrays.

For a circular perforate membrane which is vibrated around its periphery, the amplitude of vibration increases towards the centre of the perforate membrane. Thus, the central region of the perforate membrane can be regarded as an "excitation region" in which the amplitude of vibration is greater than the average amplitude of vibration for that membrane. The geometric centre, or "centroid" of the perforate membrane is generally where the amplitude of vibration is at its greatest value. Thus, the centroid and its immediate surroundings can be regarded as the "maximum excitation region" of the perforate membrane. By positioning both of the first and second arrays in the central region of the perforate membrane, the number of apertures of the first and second arrays which are vibrated to above the ejection threshold can be maximised to increase the flow of droplets generated for a given mode of vibration. This can reduce the power requirements of the aerosol delivery system for a given flow rate and can be particularly beneficial when the apertures of one or both of the first and second arrays are small in size.

In this example, the first and second arrays are coincident. As such, there is 100 percent overlap between the two arrays. However, in other examples, the degree of overlap can be less. This will reduce the proportion of small droplets which are entrained into the flow of large droplets but can still provide substantial benefits from delayed evaporation of the small droplets which are entrained.

Figure 7:
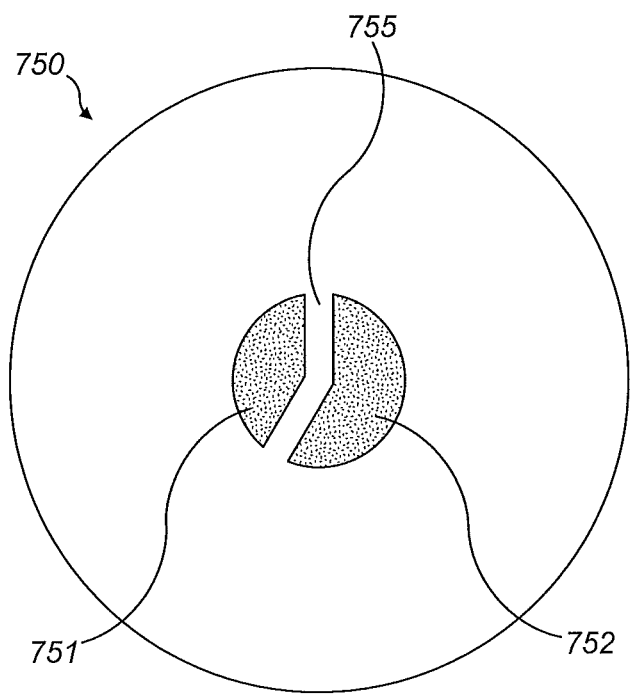
FIG. 7 is a schematic end view of a second embodiment of perforate membrane for the aerosol delivery system of FIG. 1 or for the cartridges of any of FIGS. 2 to 5.

FIG. 7 is a schematic end view of a second embodiment of perforate membrane 750. As with the first embodiment of membrane 650, perforate membrane 750 includes a plurality of apertures arranged in a first array 751 of apertures and a second array 752 of apertures. However, unlike with the perforate membrane 650 of the first embodiment, the first and second arrays 751, 752 do not overlap. Instead, the apertures of the first array 751 are grouped together in a first discrete region of the perforate membrane 750 and the apertures of the second array 752 are grouped together in a second discrete region of the perforate membrane 750. The first and second discrete regions are separated from each other by an intermediate region 755 of the perforate membrane, which may be unperforated. Thus, the apertures of the first and second arrays 751, 752 are not mixed or intermingled. The apertures of the first array 751 have a first configuration and the apertures of the second array 752 have a second configuration which is different from the first configuration. The different configurations allows the first array to generate droplets having a different size distribution to those generated by the second array. The "configuration" of the apertures may refer to their shape, dimensions, cross-sectional profile, or to the spacing between adjacent apertures. In this example, the spacing, shape, and cross-section profile of the apertures of the first and second arrays are generally the same. However, the apertures of the first array 751 are formed with a first aperture size while the apertures of the second array 752 are formed with a second aperture size which is greater than the first aperture size.

Preferably, the apertures of the first array have an average hydraulic diameter of less than 5 microns, for example in the range of 2 to 5 microns. This generates droplets of 5 microns or less in diameter. Such droplets have been found to be beneficial for uptake of medicament in the lungs of a user for a given flow rate. Preferably, the apertures of the second array have an average hydraulic diameter of at least 5 microns, preferably from 5 microns to 15 microns. This has been found to be particularly effective at generating droplet sizes of 10 microns or larger, for example up to 30 microns in diameter. Such droplet sizes have been found to be beneficial for flavour delivery and mouth feel.

This different "configuration" means that the droplets generated by the first array tend to be smaller than those generated by the second array. The range of droplet sizes generated by the first and second arrays can be further distinguished from each other by arranging the apertures of the first array with a first spacing between adjacent apertures and arranging the apertures of the second array with a second spacing between adjacent apertures, which is different to the first spacing.

By arranging the first and second arrays in discrete regions, the aperture size of each array can be tuned according to properties of the liquid formulation or formulations in fluid contact with those discrete regions and according to the desired aerosol properties. Where the perforate membrane 750 is used in a cartridge having first and second reservoir portions separated by a liquid barrier, as described above in relation to FIGS. 2 to 5, the first array is preferably in fluid contact with the opening of the first reservoir portion and the second array is preferably in fluid contact with the second reservoir portion. The position of the liquid barrier may correspond with the position of the intermediate region 755 between the first and second arrays 751, 752. Thus, separating the different regions of apertures allows fluid feed arrangements in the cartridge to deliver different liquid formulations to the different aperture types.

Figure 8:
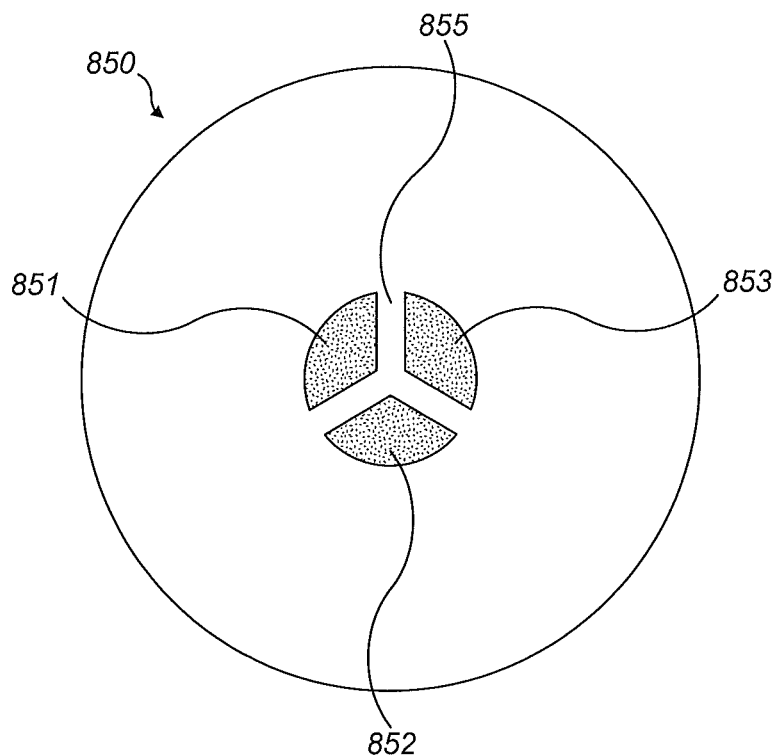
FIG. 8 is a schematic end view of a third embodiment of perforate membrane for the aerosol delivery system of FIG. 1 or for the cartridges of any of FIGS. 2 to 5.

FIG. 8 is a schematic end view of a third embodiment of perforate membrane 850. As with the second embodiment of membrane 750, perforate membrane 850 includes a plurality of apertures arranged in a first array 851 of apertures in a first discrete region, and a second array 852 of apertures in a second discrete region. Again, the apertures of the first array 851 have a first configuration and the apertures of the second array 852 have a second configuration which is different from the first configuration. Perforate membrane 850 further includes a third array 853 of apertures in a third discrete region, the third array 853 of apertures having a third configuration which may be different to both of the first and second configurations. This arrangement allows greater variety in the droplet size distribution generated by the perforate membrane. It may also be particularly useful if used in conjunction with a cartridge having a fluid reservoir with three reservoir portions, since it allows fluid feed arrangements in the cartridge to delivery different liquid formulations to the three different aperture types, as will be readily understood by the skilled person.

Figure 9:
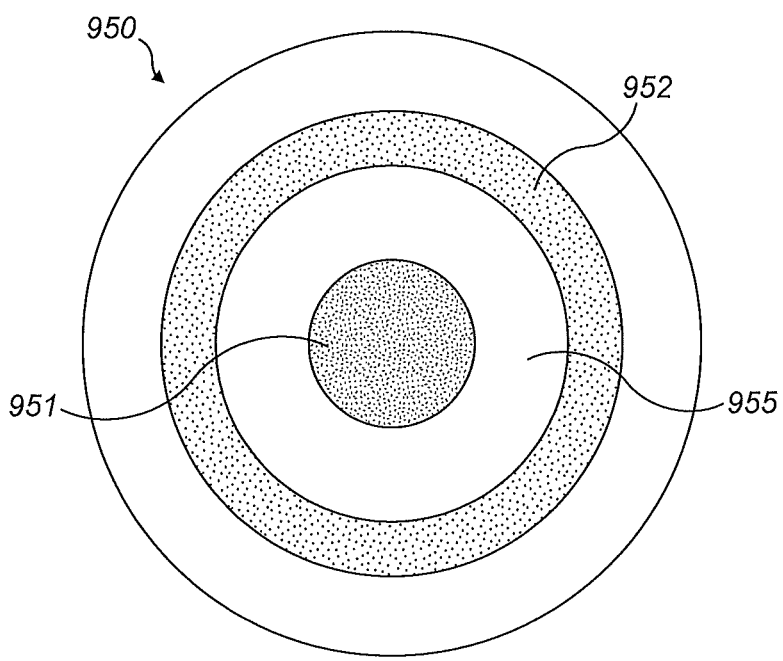
FIG. 9 is a schematic end view of a fourth embodiment of perforate membrane for the aerosol delivery system of FIG. 1 or for the cartridges of any of FIGS. 2 to 5.

FIG. 9 is a schematic end view of a fourth embodiment of perforate membrane 950. As with the membrane 750 of the second embodiment, the perforate membrane 950 includes a plurality of apertures arranged in a first array 951 of apertures with a first configuration and a second array 952 of apertures with a second configuration. Again, the apertures of the first array 951 are grouped together in a first discrete region of the perforate membrane 950 and the apertures of the second array 952 are grouped together in a second discrete region of the perforate membrane 950, the first and second discrete regions being separated from each other by an intermediate region 955 of the perforate membrane, which may be unperforated. In this example, the first array 951 is disposed in a central region of the perforate membrane and the second array 952 is disposed around the first array 951 towards the periphery of the perforate membrane 950. This configuration is of particular benefit for cartridges in which the fluid reservoir comprises a first reservoir portion positioned along the central axis of an annular second reservoir portion, as illustrated in FIGS. 2 to 5.

Typically, the mode of vibration of the membrane is such that different regions of the membrane vibrate with different amplitudes such that acceleration and pressure in the fluid in those regions is different. With the configuration shown, the apertures of the first array 951 are located in a first discrete region which is in an excitation region of the perforate membrane and the apertures of the second array 952 are not. Thus, the first discrete region and therefore the apertures of the first array vibrate with a greater amplitude than the second discrete region and the apertures of the second array, such that acceleration and pressure in the fluid in contact with the first array is greater than that in the fluid in contact with the second array.

By configuring the apertures of the first and second arrays differently and locating the first and second arrays in first and second discrete regions having different vibration characteristics, the generation of droplets can be tuned to the preferred performance. This is illustrated in the table below in which the different permutations of aperture size and aperture spacing for first and second arrays with different configurations are compared and their relevant application and resulting performance is discussed. In the below table, the terms "small" and "big" are used to describe the relative aperture sizes and the terms "Dense" and "Well-spaced" are used to describe the spacing between adjacent apertures in each array. By way of illustration, the term "small" may refer to apertures having a diameter of less than 5 microns and the term "big" may refer to apertures having a diameter of 5 microns or more. Similarly, the term "dense" may refer to an arrangement in which a spacing of less than 75 microns, for example less than 65 microns, is provided between adjacent apertures, and the term "well-spaced" may refer to an arrangement in which a spacing of more than 75 microns is provided between adjacent apertures. Although this table is discussed with reference to the embodiment of perforate membrane shown in FIG. 9, it is applicable to any perforate membrane having a first array of apertures with a first configuration in a first discrete region, and a second array of apertures with a second configuration in a second discrete region, where the first and second discrete regions have different vibration characteristics.

TABLE 1

Combinations of aperture sizes and spacing

| | First Array (Higher accel.) | | Second Array (Lower accel.) | | |
|---|---|---|---|---|---|
| | Spacing | Size | Spacing | Size | Further Details |
| 1 | Dense | Small | Dense | Big | Small holes in vibrationally active first discrete region generates higher flow of small droplets. For both arrays, the density of holes is such that droplets coalesce to make larger droplets after ejection. Configuring the first array with small holes in a more active area of the vibrating mesh can help with ensuring a higher percentage of the holes are above the ejection threshold as smaller holes will tend to have a higher vibration ejection threshold. |
| 2 | Dense | Big | Dense | Small | Large holes in vibrationally active first discrete region generates higher flow of large droplets. For both arrays, the density of holes is such that droplets coalesce to make larger droplets after ejection. Configuring the first array with large holes in a more active area of the vibrating mesh can help with ensuring a higher percentage of the holes are above the ejection threshold to maximise delivery of larger droplets |
| 3 | Well-spaced | Small | Well-spaced | Big | Small holes in vibrationally active first discrete region generates higher flow of small droplets by ensuring a higher percentage of the small holes are above the ejection threshold, which tends to be higher than for larger holes. Spacing of apertures of both arrays is such that droplets tend not to coalesce to make larger droplets. |
| 4 | Well-spaced | Big | Well-spaced | Small | Large holes in vibrationally active first discrete region generates higher flow of large droplets by ensuring a higher percentage of the holes are above the ejection threshold to maximise delivery of larger droplets. This may be particularly useful when the larger holes need to be in a more active region, such as for a higher viscosity fluid. Spacing of apertures of both arrays is such that droplets tend not to coalesce to make larger droplets. |
| 5 | Well-spaced | Small | Dense | Small | Small holes in vibrationally active first discrete region generates higher flow of small droplets by ensuring a higher percentage of the small holes are above the ejection threshold, which tends to be higher than for larger holes, and spacing the apertures such that they tend not to coalesce. Smaller droplets generated in second array do tend to coalesce into larger droplets, in part due to the density of hole spacing and in part due to the lower vibrational activity of the mesh in the second discrete region. If a flavour formulation is supplied to the second array and a nicotine formulation is supplied to the first array, then this configuration allows targeted delivery to the mouth and lung, respectively. |
| 6 | Well-spaced | Small | Dense | Big | Same as 5 above for the first array. Second array allows creation of higher volumes of large droplets where the lower vibrational activity is sufficient to overcome the lower ejection threshold typical of larger holes. |
| 7 | Well-spaced | Big | Dense | Small | More vibrationally active first array generates large droplets that tend not coalesce and less active second array |

TABLE 1-continued

| Combinations of aperture sizes and spacing | | | | | |
|---|---|---|---|---|---|
| | First Array (Higher accel.) | | Second Array (Lower accel.) | | |
| | Spacing | Size | Spacing | Size | Further Details |
| | | | | | generates small droplets which do tend to coalesce. This would result in droplet sizes being more similar, but the larger droplets formed by coalesce can have less momentum and so be delivered to a different area. This has application for delivering different formulations to different areas of the mouth, so flavours can be targeted at their flavour receptors and so providing a higher response for a given amount of flavour formulation |
| 8 | Well-spaced | Big | Dense | Big | More vibrationally active first array generates large droplets that tend not coalesce and second array generates large droplets which do tend to coalesce. This would result in droplet sizes being differentiated despite being generated by the same size hole. Generating larger droplets by coalesce can help with preventing leakage which may occur in larger holes, for example holes larger than 50-micron diameter with lower surface tension e.g. 30 mPa-s. |
| 9 | Dense | Small | Well-spaced | Small | More vibrationally active first array generates small droplets that tend to coalesce due to the density of holes. Having small holes to indirectly generate larger droplets is helpful in the case of low surface tension fluids that are difficult to control and prevent leakage from larger holes. For the second array, where the holes are well-spaced the droplets tend not to coalesce. If a nicotine or similar formulation is supplied to the second array and a flavour formulation is supplied to the first array then this could allow targeted delivery to the lung and mouth respectively. |
| 10 | Dense | Small | Well-spaced | Big | Same as 9, above, for the first array. For second array, large droplets will tend to coalesce into even larger droplets due to hole density and the fact that the second array is in a less active region of the membrane, which exaggerates the effect. Using larger holes for larger droplets could for example be useful for high viscosity flavour formulations so that the ejection threshold is reduced compared to with a small hole. |
| 11 | Dense | Big | Well-spaced | Small | Large holes in vibrationally active first discrete region generates higher flow of large droplets which tend to coalesce. Second array generates small droplets which tend not to coalesce. |
| 12 | Dense | Big | Well-spaced | Big | Large holes in vibrationally active first discrete region generates higher flow of large droplets which tend to coalesce. Second array generates large droplets which tend not to coalesce. This results in droplet sizes being differentiated despite being generated by the same size hole. Generating larger droplets by coalescence can help with preventing leakage which may occur in larger holes, for example holes larger than 50-micron diameter with lower surface tension e.g. 30 mPa-s so if |

TABLE 1-continued

Combinations of aperture sizes and spacing

| First Array (Higher accel.) | | Second Array (Lower accel.) | | |
|---|---|---|---|---|
| Spacing | Size | Spacing | Size | Further Details |
| | | | | different formulations are supplied to the first and second arrays then these formulations can be targeted at different areas of the mouth. |

Figure 10:
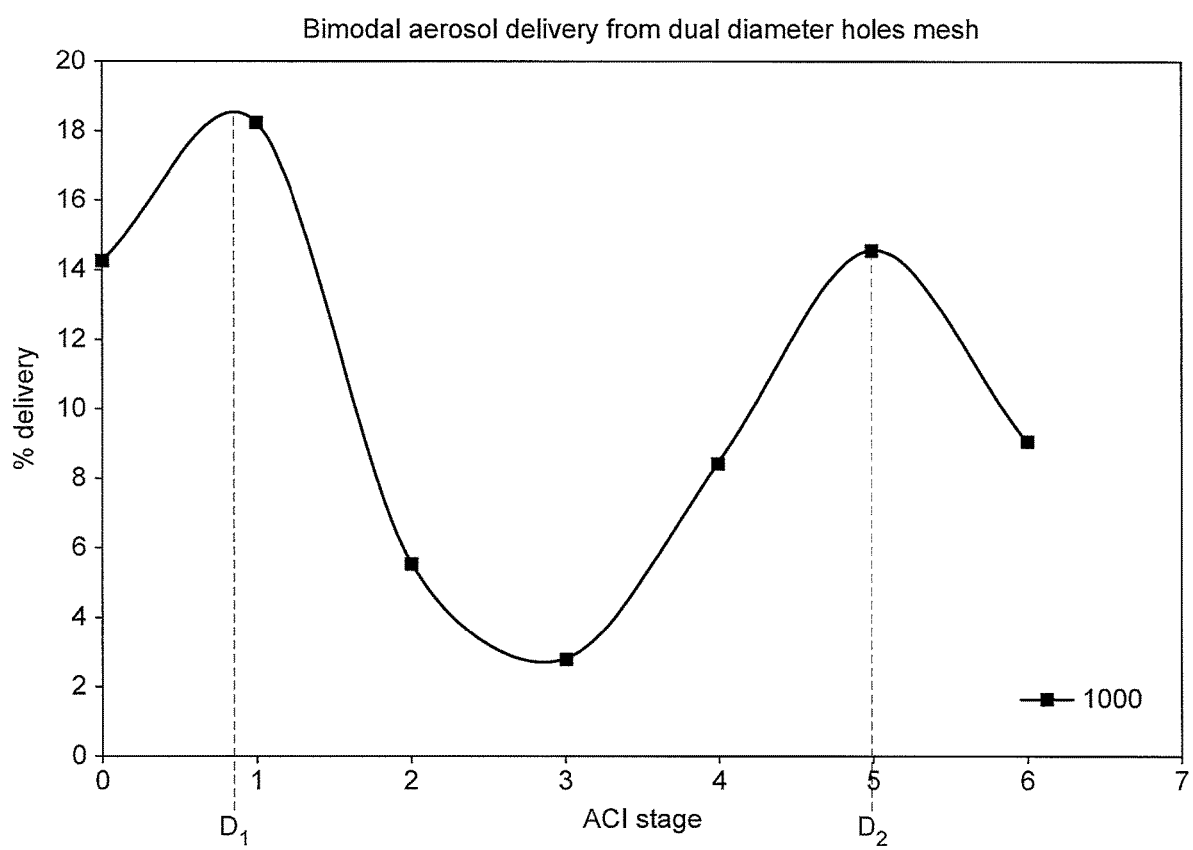
FIG. 10 shows the calculated droplet size distribution from the fourth embodiment of perforate membrane of FIG. 9 when used in the aerosol delivery system of FIG. 1.

FIG. 10 shows the calculated droplet size distribution from the fourth embodiment of perforate membrane 950, in which the apertures of the first array have a diameter of 3 microns, the apertures of the second array have a diameter of 12 microns, and the apertures of both arrays are spaced by more than 75 microns. As can be seen, the trace 1000 illustrates the simultaneous generation of a dual droplet size distribution in which droplet size is concentrated around two different droplet sizes D1 and D2. The ACI stage reference on the Y axis refers to the stage of an Anderson Cascade Impactor which is used to characterise droplet streams by collecting particles on a series of stages where the flow path in the impactor is arranged such that larger particles are captured on earlier stages and smaller particles on later stages. At 28.3 litres per minute of flow through an Anderson Cascade Impactor the cut off levels (microns) for the stages are: stage 0: 9.0, stage 1: 5.8, stage 2: 4.7, stage 3: 3.3, stage 4: 2.1, stage 5: 1.1, stage 6: 0.7, stage 6: 0.4

There are a number of different methods by which the apertures in the perforate membranes can be formed. For example, the apertures can be formed by electroforming the membrane, or by laser drilling.

Electroforming typically involves over growing nickel based alloys over a smooth substrate with a pattern of photo resist spots used to define the pattern of holes, as carried out by Veco B. V. Eerbeek, of The Netherlands. The size of the holes is then typically a function of the thickness of material grown over the resist spots. However, this method may make it difficult to control hole size, especially for smaller holes. The strong dependency on the thickness of deposited material means that the tolerance for small holes is relatively broad. A second issue is that forming two size holes at the same time is inconsistent as this will depend on the size of resistance spot applied and the thickness of deposited plating. This means that the process control has the challenge of controlling two variables with only one control parameter, thickness, further leading to yield issues. This process also has a limited choice of materials which can be used with some robustness and compatibility issues. As above the overgrowing method of forming small holes is problematic but there is an alternative of using a thick resist method where the hole size is defined by the photo resist, or photo-defined hole size. In its simplest form this allow formation of parallel sided holes where their diameter is defined by the photo resist pattern, which in turn allows a range of hole sizes to be formed at the same time. The combination of using two resist layers such that one defines a larger hole and the second layer defines a smaller hole. In this way a stepped hole with parallel sides can be defined. While this provides an approximation of the preferred hole geometry the parallel sides are a significant compromise for the fluid dynamic properties of the hole and the resist patterning and alignment adds complexity to the process.

Laser Drilling provides an alternative method for forming perforate membranes with well controlled distributions of hole sizes in the target size range. Control of the laser power, number of pulses, focal position, and focal length of the final objective allows independent control of the hole size and profile for two or more target hole sizes. This technique offers the choice of a much greater range of materials including many metals, ceramics and polymer materials. Different thicknesses of materials can be selected and the drill parameters adapted to suit the material thickness. This allows decoupling of the holes size, pitch and material thickness compared to the process limitations of electroforming. This can help the design of the perforate membrane as it allows tuning of the mechanical vibrational behaviour to the preferred frequency of operation and so optimising the resonant behaviour. This control is dominated by the thickness and geometry of the perforate membrane. Material selection also allows perforate membranes to be formed into a domed or other out or plane shape and the combination of formable materials, geometry and material thickness greatly enhance design freedom and optimisation for vibration across a wide area of perforate membrane and so maximising the area with sufficient vibration to generate droplets and so with a suitable hole pattern maximise delivery rate of the chosen droplet sizes.

Using a higher power and larger spot size allows larger holes to be formed and similarly using a lower power and tightly focussed small spot size allows small holes to be formed. Drilling a population of two different hole sizes requires switching between the two different drilling parameters. This can be achieved in a number of ways; simply changing the control parameters for a single laser, switching between two laser systems within the same overall drilling instrument, or by drilling the two or more distributions on separate drilling instruments.

The preference between these approaches is largely driven by the target throughput and trade-off between process stability and part handling. Typically having a fixed set of parameters for the different hole size populations is preferred for process stability and consistency so using either two laser light paths in one instrument or using two separate instruments may be preferred.

The invention claimed is:

1. A cartridge for an aerosol delivery system, the cartridge comprising:
    a fluid reservoir including a first reservoir portion for containing a first liquid, a second reservoir portion for containing a second liquid different to the first liquid, and at least one liquid barrier configured to separate the first and second reservoir portions, wherein the first and second reservoir portions have respective first and second openings at a first end of the cartridge; and
    a perforate membrane located at the first end of the cartridge and extending over both of the first and second openings such that a first side of the perforate membrane is in fluid communication with the first and second openings, the first and second openings being configured to supply the first and second liquids to the perforate membrane during use, the perforate membrane comprising a plurality of apertures configured to eject one or both of the first and second liquids from a second side of the perforate membrane in the form of liquid droplets when the perforate membrane is vibrated during use, wherein the second reservoir portion is annular so as to define a ring shape that defines a cavity in which the first reservoir portion is disposed.

2. The cartridge according to claim 1, wherein the plurality of apertures comprises a first array of apertures of a first configuration and a second array of apertures of a second configuration which is different to the first configuration.

3. The cartridge according to claim 2, wherein the first array of apertures is located in a first discrete region of the perforate membrane and the second array of apertures is located in a second discrete region of the perforate membrane.

4. The cartridge according to claim 3, wherein the first reservoir portion is in fluid communication with the first array of apertures in the first discrete region via the first opening, wherein the first opening is separated from at least some apertures of the second array of apertures in the second discrete region by the at least one liquid barrier, wherein the second reservoir portion is in fluid communication with the second array of apertures in the second discrete region via the second opening, and wherein the second opening is separated from at least some apertures of the first array of apertures in the first discrete region by the at least one liquid barrier.

5. The cartridge according to claim 3, wherein the first discrete region is located in an area of the perforate membrane having a first vibration characteristic and the second discrete region is located in another area of the perforate membrane having a second vibration characteristic which is different to the first vibration characteristic, such that vibration of the perforate membrane during use causes the first discrete region to vibrate at a different amplitude than the second discrete region, and wherein the first array of apertures is located in or adjacent to a central area of the perforate membrane and the second discrete region is located peripherally of the first discrete region.

6. The cartridge according to claim 2, wherein the apertures of the first array are of a first aperture size and the apertures of the second array are of a second aperture size, wherein the first and second aperture sizes are different.

7. The cartridge according to claim 2, wherein a majority of the apertures of the first array each have a hydraulic diameter at the second side of the perforate membrane of at least 0.5 microns and less than 5 microns.

8. The cartridge according to claim 2, wherein a majority of the apertures of the second array each have a hydraulic diameter at the second side of the perforate membrane of at least 5 microns.

9. The cartridge according to claim 2, wherein a majority of the apertures of the first array are spaced, at the second side of the perforate membrane, from any adjacent aperture by a first spacing and a majority of the apertures of the second array are spaced, at the second side of the perforate membrane from any adjacent aperture by a second spacing which is different to the first spacing.

10. The cartridge according to claim 2, wherein a majority of the apertures of the first array each have a hydraulic diameter at the second side of the perforate membrane of at least 1 micron and less than 5 microns.

11. The cartridge according to claim 2, wherein a majority of the apertures of the first array each have a hydraulic diameter at the second side of the perforate membrane of at least 2 microns and less than 5 microns.

12. The cartridge according to claim 2, wherein a majority of the apertures of the second array each have a hydraulic diameter at the second side of the perforate membrane from 5 to 60 microns.

13. The cartridge according to claim 2, wherein a majority of the apertures of the second array each have a hydraulic diameter at the second side of the perforate membrane from 5 to 50 microns.

14. The cartridge according to claim 2, wherein a majority of the apertures of the second array each have a hydraulic diameter at the second side of the perforate membrane from 5 to 15 microns.

15. The cartridge according to claim 1, wherein the at least one liquid barrier comprises a resilient seal in contact with the first side of the perforate membrane.

16. The cartridge according to claim 1, wherein at least one of the first and second reservoir portions comprises a porous carrier material adjacent to the perforate membrane.

17. The cartridge according to claim 1, wherein the first reservoir portion contains a liquid formulation comprising nicotine, and wherein the second reservoir portion contains a liquid formulation comprising one or more flavour compounds.

18. An aerosol delivery system comprising:
the cartridge according to claim 1,
an aerosol delivery device with which the cartridge is configured to be removably coupled, the aerosol delivery device comprising actuation means configured to vibrate the perforate membrane to cause the first and second liquids in the first and second reservoir portions to be ejected as liquid droplets from the second side of the perforate membrane.

* * * * *